US00PP08067P

United States Patent [19]

Gerawan

[11] Patent Number: Plant 8,067

[45] Date of Patent: Dec. 22, 1992

[54] PRIMA BLACK PLUM 5-25

[76] Inventor: Michael R. Gerawan, 6407 S. Englehart, Reedley, Calif. 93654

[21] Appl. No.: 632,521

[22] Filed: Dec. 24, 1990

[51] Int. Cl.[5] ..... A01H 5/00
[52] U.S. Cl. ..... Plt./38.1
[58] Field of Search ..... Plt./38

*Primary Examiner*—James R. Feyrer

*Attorney, Agent, or Firm*—Worrel & Worrel

[57] ABSTRACT

A new and distinct variety of plum tree producing fruit which are mature for harvesting and shipment approximately June 1 in the San Joaquin Valley of central California approximately five to seven days before "Black Beaut" plum tree and which are very slightly rounded with a mild taste and distinct aroma with good shipping and handling characteristics.

1 Drawing Sheet

BACKGROUND OF THE NEW VARIETY

The present invention relates to a new and distinct variety of plum tree, which will hereinafter be denominated varietally as the "Prima Black Plum 5-25" plum tree, and more particularly to a plum tree which produces fruit of a dark mulberry coloration having flesh with a distinct aroma and which is mature for harvesting and shipment approximately June 1 in the San Joaquin Valley of central California, or approximately five to seven days before the "Black Beaut" plum tree.

The development of new varieties of fruit trees having superior characteristics is a pursuit requiring painstaking effort over many years and often involving many thousands of seedlings. In such developmental work, an experienced plant breeder must independently monitor the development of the seedlings recording all of the pomological details thereof and noting the characteristics by comparison to the best of other known varieties as to a host of criteria. Out of many thousand such seedlings and after years of effort, the breeder may be considered fortunate to be able to select one or two of the new varieties of sufficient promise for further development.

In the case of the new variety of the present invention, superior attributes were observed in a number of significant respects causing its selection for further development. The "Prima Black Plum 5-25" plum tree produces a clingstone fruit having an attractive dark mulberry coloration, a pleasingly round and symmetrical form and a flesh having a distinctive aroma and mild flavor. The fruit is mature for harvest in the period between the fruit of the "Red Beaut" plum tree and the "Black Beaut" plum tree, or about June 1 in the San Joaquin Valley of central California.

ORIGIN AND ASEXUAL REPRODUCTION OF THE NEW VARIETY

The present variety of plum tree hereof was discovered in 1984 by the inventor as an open pollinated seedling of unknown parentage growing in a cultivated area on Ranch 15 owned by Ray and Star Gerawan in Sanger in the San Joaquin Valley of central California. The new variety was selected as the result of a mass breeding program. The seedling was selected from this program, but its parentage is unknown. Seeds collected for the mass breeding program came from several ranches encompassing nearly five thousand acres growing many varieties of tree fruit. No effort was made to retain the specific pedigree of any particular seed lot. The new variety of plum tree was asexually reproduced by the inventor budding and grafting test tree with scions of the new variety on the same property. Subsequently the inventor observed the test trees over several growing seasons and confirmed that the progeny have characteristics which are identical to those of the parent tree.

SUMMARY OF THE NEW VARIETY

The "Prima Black Plum 5-25" plum tree is characterized as to novelty by producing clingstone fruit which is of a rounded, symmetrical form having an attractive dark mulberry coloration, a juicy mild flavor with a distinctive aroma and which is ripe for commercial harvesting and shipment approximately June 1 in the San Joaquin Valley of central California.

BRIEF DESCRIPTION OF THE DRAWING

The accompanying drawing is a photograph showing the plum tree of the new variety including fruit of the new variety sectioned, one with the stone removed to expose the pit cavity and the other with the stone left in place; a second in side elevation showing the suture thereof; a third in top plan view showing the apex end thereof; and a fourth in bottom plan view showing the base thereof; and representative foliage of the new variety.

DETAILED DESCRIPTION

Referring more specifically to the pomological details of this new and distinct variety of plum tree, the following has been observed under the ecological conditions prevailing at a ranch which is located in Sanger, Calif. All major color code designations are by reference to the Dictionary of Color, by Maerz and Paul, First Edition, 1930. Common color names are also employed occasionally.

TREE

Generally:

*Size.*—Medium.

*Figure.*—Upright. The subject variety is upright to upright-spreading in form and relatively dense. The asexually reproduced trees of the new variety were pruned in a standard vase-shaped configuration.

*Productivity.*—Productive.
*Regularity of bearing.*—Productive.
Trunk:
*Size.*—Stocky.
*Surface texture.*—Medium shaggy.
Branches:
*Size.*—Medium.
*Surface texture.*—Rough.
*Color.*—Base Color — Page 39, Plate 8, E-9, Negro. Streak Color — Page 45, Plate 11, D-11, Ponce de Leon.
*Lenticels.*—Numerous. Size — 1 mm (0.03937 inches) to 2 mm (0.07874 inches) by 4 mm (0.15748 inches) to 8 mm (0.31496 inches).

LEAVES

Size:
*Generally.*—Medium. Leaf surface — Rugose. Leaf stipules — Number — Two at base of petiole. Lanceolate in form.
*Average length.*—82 mm (3.28 inches) to 90 mm (3.6 inches).
*Average width.*—31 mm (1.24 inches) to 40 mm (1.6 inches).
Form: Ovate.
Color:
*Upwardly disposed surface.*—Page 69, Plate 23, J-7, Cypress Green+.
*Downwardly disposed surface.*—Page 67, Plate 22, E-6, Palmetto.
Marginal form: Double serrate.
Glandular characteristics: 1 to 2, opposite when two globose, reddish brown.
Petiole:
*Length.*—12 mm (0.48 inches) to 14 mm (0.56 inches).
*Thickness.*—2 mm (0.08 inches).
Stem glands:
*Number.*—Variable, one to six in number.
*Arrangement.*—Opposite and alternate.
*Type.*—Globose.
*Size.*—Small.
*Color.*—Reddish Brown.

FLOWERS

The following description was prepared from bloom taken from trees of the subject variety growing in a test planting near Sanger, Calif. in early March, 1992. The number of chilling hours below 45 degrees Fahrenheit in this tree fruit growing area of Fresno County, California in the 1991–1992 winter season was nearly 1200 hours. This represents an above average accumulation of cold hours for this location.

Flower buds:
*Size.*—Small. Conic in form, plump and slightly appressed to the stem. The buds are hardy under typical climatic conditions in the San Joaquin Valley of California.
*Surface texture.*—Glabrous.
*Shape.*—Obtuse.
*Scales.*—Color — Medium Brown (Chestnut Brown 7-E-10).
Pedicel: Short.
Stamens: Numerous.
Pistil: One.

Date of bloom: Two to three days after "Red Beaut" plum tree and about the same as "Blackamber" plum tree. The bloom is very early in timing in relation to other standard plum tree varieties and appropriately with such other varities of plum trees as the "Ambra" plum tree. In 1992, the date of first bloom was February 20 and the date of full bloom was February 27. No pollination tests have been conducted, but it is believed the new variety requires pollination as in conventional varieties. This is achieved by proximity to other varieties blooming at the same time such as the "Ambra" plum tree.
Flower:
*Size.*—Medium to above average.
*Diameter.*—Fully expanded averages from 24 mm (0.9448 inches) to 26 mm (1.023 inches).
Bloom.
*Quantity.*—Abundant.
Flower buds:
*Number.*—Variable from 2 to 4 per node.
Petals:
*Number.*—Five.
*Size.*—Large.
*Length.*—Averaging from 11 mm (0.4330 inches) to 12 mm (0.4724 inches).
*Width.*—8 mm (0.3149 inches) to 8.5 mm (0.3346 inches).
*Shape.*—Ovate.
*Color.*—White (1-A-1).
Petal claw:
*Form.*—Short and Truncate.
Petal margins: Moderately undulate, slightly more at the petal apices.
Petal apices: Most frequently obtuse.
Pedicel:
*Length.*—Medium. From 7.5 mm (0.2952 inches) to 8.5 mm (0.3346 inches).
*Thickness.*—Averages 1.0 mm (0.0393 inches).
*Color.*—Light green (18-I-3).
Pedicel surface: Glabrous.
Calyx:
*Surface.*—Glabrous.
*Color.*—Light green (20-H-1) with a slight brownish caste.
Nectaries:
*Color.*—Dark orange-brown (Windsor Tan 13-G-12), becoming more dull in finish with age.
Anthers:
*Size.*—Medium.
*Color.*—Gold yellow (Narcissus yellow 10-K-4) ventrally, but with a red-orange (Coral Red 2-I-10) tinge dorsally along the anther margins.
Pollen: Abundant.
*Color.*—Yellow (Apricot yellow 9-K-5).
Stamens:
*Length.*—Variable. Stamens are almost always shorter than the pistil. From 6 mm (0.2362 inches) to 8 mm (0.3149 inches).
*Color.*—White (1-A-1).
Pistil:
*Surface.*—Glabrous.
*Length.*—Averages 11 mm (0.4330 inches) including the ovary.
*Color.*—Light green (17-I-2).

FRUIT

Maturity when described: Ripe for commercial harvesting and shipment approximately June 1 near Sanger, Calif., about four to six days after "Red Beaut" plum tree and about five to seven days in advance of "Black Beaut" plum tree. The new variety requires thinning as in other varieties of plum trees.

Size:

*Average diameter.*—52 mm (2.08 inches) to 57 mm (2.28 inches).

*Average diameter transverse in the suture plane.*—46 mm (1.84 inches) to 52 mm (2.08 inches).

*Average diameter transverse and at right angles to the suture plane.*—43 mm (1.72 inches) to 50 mm (2.0 inches).

Form:

*Uniformity.*—Uniform.

*Symmetry.*—Round, symmetrical.

Suture:

*Generally.*—Distinct and extends from base to apex.

*Length.*—74 mm (2.96 inches) to 78 mm (3.12 inches).

Ventral surface:

*Generally.*—Smooth.

Stem cavity:

*Generally.*—Acuminate.

*Depth.*—8 mm (0.32 inches) by 12 mm (0.48 inches) by 10 mm (0.4 inches).

Stem:

*Caliper.*—2 mm (0.08 inches).

*Caliper — length.*—14 mm (0.56 inches).

Apex:

*Shape.*—Variable, some flat and some slightly rounded.

Base: Very slightly rounded.

Pistil point: Some depressed, some slightly pointed.

Skin:

*Thickness.*—Medium.

*Texture.*—Medium.

*Tendency to crack.*—None.

*Color.*—Page 119, Plate 48, E-90, Mulberry.

*Pubescence.*—None.

Flesh:

*Color — near skin.*—Page 31, Plate 4, L-10, Holly Berry.

*Color — near pit.*—Page 43, Plate 10, J-7, Mirabelle.

*Surface of pit cavity.*—Rough after pit removal.

*Color of pit well.*—Page 43, Plate 10, J-7, Mirabelle.

*Amygdalin.*—None.

*Juice production.*—Juicy.

*Flavor.*—Subacid, mild. The fruit of the subject variety is sweet with moderate acidity. The fruit is well balanced and of high quality.

*Aroma.*—Distinct.

*Texture.*—Meaty.

*Fibers.*—Moderate.

*Ripening.*—Even.

*Eating quality.*—Good.

Stone:

*Attachment.—Clingstone.*

*Fibers.*—Many.

*Size — length.*—20 mm (0.8 inches) to 21 mm (0.84 inches).

*Size — width.*—17 mm (0.68 inches) to 19 mm (0.76 inches).

*Size — thickness.*—8 mm (0.32 inches) to 9 mm (0.36 inches).

*Form.*—Generally — Oval, flattened at base and pointed at apex.

*Color.*—Page 43, Plate 10, J-7, Mirabelle.

*Base— Shape.—Flat.*

*Sides.*—Generally — Two to three ridges per side, some extending from base to apex and others extending only part way.

*Ridges.*—Jagged.

*Size of position of grooves.*—None.

*Dorsal edge.*—Narrow with slight groove throughout.

*Ventral edge.*—Thin.

*Tendency to split.*—None.

Use: Fresh.

Keeping quality: Good.

Shipping and handling qualities: Good.

Although the new variety of plum tree possesses the described characteristics noted above as a result of the growing conditions prevailing near Sanger in the central San Joaquin Valley of California, it is to be understood that variations of the usual magnitude and characteristics incident to changes in growing conditions, fertilization, irrigation, pruning and pest control are to be expected.

Having thus described and illustrated my new variety of plum tree, what I claim as new and desire to be secured by Plant Letters Patent is:

1. A new and distinct variety of plum tree substantially as illustrated and described and which produces a clingstone fruit of a mulberry skin coloration which are mature for commercial harvesting and shipment approximately June 1 in the San Joaquin Valley of central California approximately five to seven days before the "Black Beaut" plum tree and about four to six days after the "Red Beaut" plum tree.

* * * * *

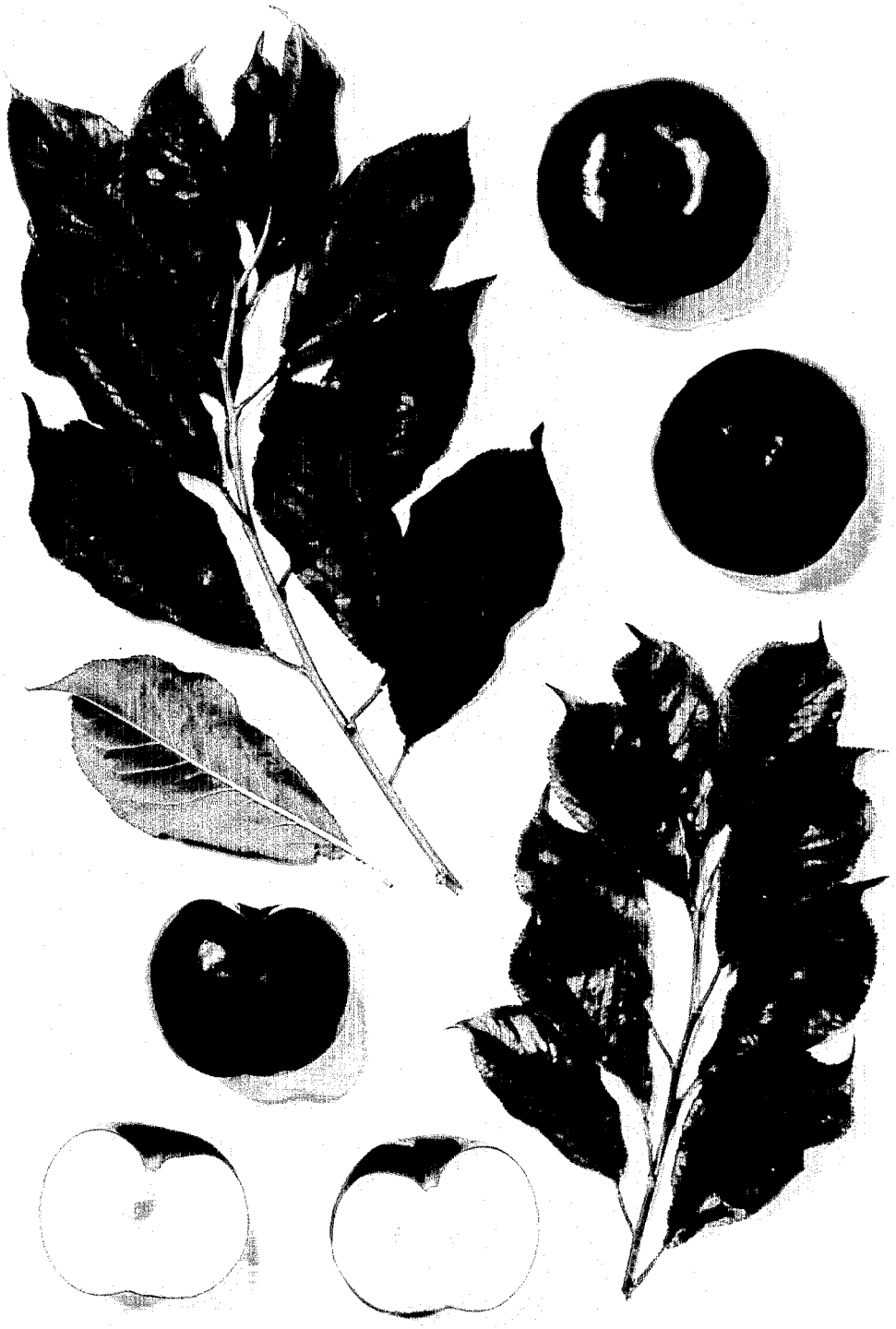

UNITED STATES PATENT AND TRADEMARK OFFICE

CERTIFICATE OF CORRECTION

PATENT NO. : Plant 8,067

DATED : December 22, 1992

INVENTOR(S) : Michael R. Gerawan

It is certified that error appears in the above-identified patent and that said Letters Patent is hereby corrected as shown below:

Column 2, Line 3, delete "tree" and substitute ---trees---.

Column 4, Line 4, delete "appropriately" and substitute ---approximately---.

Signed and Sealed this

Nineteenth Day of October, 1993

Bruce Lehman

*Attest:*

BRUCE LEHMAN

*Attesting Officer*

*Commissioner of Patents and Trademarks*